(12) United States Patent
Rayhanabad

(10) Patent No.: US 10,624,631 B1
(45) Date of Patent: Apr. 21, 2020

(54) SURGICAL SUTURE AND METHOD OF SUTURING

(71) Applicant: Simon B. Rayhanabad, Huntington Beach, CA (US)

(72) Inventor: Simon B. Rayhanabad, Huntington Beach, CA (US)

(*) Notice: Subject to any disclaimer, the term of this patent is extended or adjusted under 35 U.S.C. 154(b) by 0 days.

(21) Appl. No.: 16/188,134

(22) Filed: Nov. 12, 2018

Related U.S. Application Data

(60) Provisional application No. 62/585,471, filed on Nov. 13, 2017, provisional application No. 62/599,430, filed on Dec. 15, 2017, provisional application No. 62/633,373, filed on Feb. 21, 2018, provisional application No. 62/673,760, filed on May 18, 2018.

(51) Int. Cl.
*A61B 17/06* (2006.01)
*A61B 17/00* (2006.01)

(52) U.S. Cl.
CPC .......... *A61B 17/06004* (2013.01); *A61B 2017/00486* (2013.01); *A61B 2017/06047* (2013.01); *A61B 2017/06057* (2013.01)

(58) Field of Classification Search
CPC .......... A61B 2017/00486; A61B 2017/06047; A61B 2017/06057; A61B 2017/00477; A61B 17/00234; A61B 2017/00473; A61B 17/0625; A61B 17/0469; A61B 17/0482; A61B 17/0401; A61B 17/06066; A61B 17/06004; A61B 17/06166; A61B 2017/06052; A61B 17/04; A61B 17/128; A61B 17/10; A61B 17/0483; A61B 17/0682; A61B 2017/0488; A61B 2017/0472; A61B 17/08; A61B 17/083; A61B 17/122; A61B 2017/081; A61B 2017/088; A61B 2017/00579; A61B 17/06

See application file for complete search history.

(56) References Cited

U.S. PATENT DOCUMENTS

| | | |
|---|---|---|
| 3,462,802 A | 8/1969 | Merser |
| 4,932,962 A | 6/1990 | Yoon et al. |
| 5,222,976 A | 6/1993 | Yoon |
| 5,423,856 A | 6/1995 | Green |
| 5,490,856 A | 2/1996 | Person et al. |
| 5,713,921 A | 2/1998 | Bonutti |
| 5,735,877 A | 4/1998 | Pagedas |
| 6,641,597 B2 | 11/2003 | Burkhart et al. |

(Continued)

FOREIGN PATENT DOCUMENTS

| | | |
|---|---|---|
| CN | 102164548 A | 8/2011 |
| CN | 102274056 A | 12/2011 |

(Continued)

*Primary Examiner* — Eric J Rosen
*Assistant Examiner* — Mikail A Mannan
(74) *Attorney, Agent, or Firm* — Steven R. Vosen

(57) ABSTRACT

A surgical suture and method of suturing is described. The surgical suture includes a pair of matched fastening elements connected by a length of suture. The fastening elements have interlocking components, allowing a surgeon to adjust the tightness of the suture. Fastening element holding devices are also provided to guide the use the surgical suture. The method includes placing the fastening elements in the holding devices, threading one or both of the fastening elements through the body of the patient, and securing the surgical suture, and removing the holding devices.

24 Claims, 13 Drawing Sheets

(56) References Cited

U.S. PATENT DOCUMENTS

| | | | |
|---|---|---|---|
| 7,338,502 B2* | 3/2008 | Rosenblatt | A61B 17/0487 606/139 |
| 7,744,611 B2 | 6/2010 | Nguyen et al. | |
| 8,591,528 B2 | 11/2013 | Devens, Jr. et al. | |
| 8,672,955 B2 | 3/2014 | Nagata et al. | |
| 8,740,937 B2 | 6/2014 | Surti | |
| 9,055,940 B2 | 6/2015 | Chin | |
| 9,186,134 B2 | 11/2015 | Kostrzewski | |
| 9,220,495 B2 | 12/2015 | McClurg et al. | |
| 9,220,498 B2 | 12/2015 | Mohamed et al. | |
| 9,301,740 B2 | 4/2016 | Thielen et al. | |
| 9,398,903 B2 | 7/2016 | McClellan | |
| 9,439,643 B2 | 9/2016 | Darois et al. | |
| 9,480,473 B2 | 11/2016 | Kim | |
| 9,526,492 B2 | 12/2016 | Lombardo et al. | |
| 2009/0259251 A1* | 10/2009 | Cohen | A61B 17/06166 606/228 |
| 2010/0042116 A1 | 2/2010 | Chui et al. | |
| 2010/0113873 A1 | 5/2010 | Suzuki et al. | |
| 2012/0330356 A1 | 12/2012 | Rosenberg | |
| 2013/0226233 A1 | 8/2013 | D'Agostino et al. | |
| 2015/0018878 A1 | 1/2015 | Rizk et al. | |
| 2015/0032143 A1 | 1/2015 | Khouri | |
| 2016/0015389 A1 | 1/2016 | Belson | |
| 2016/0242772 A1 | 8/2016 | Peterson et al. | |

FOREIGN PATENT DOCUMENTS

| | | |
|---|---|---|
| EP | 0684012 A | 12/1999 |
| WO | WO9604871 A1 | 2/1996 |
| WO | WO9641581 A1 | 12/1996 |
| WO | WO2010108050 A2 | 9/2010 |

\* cited by examiner

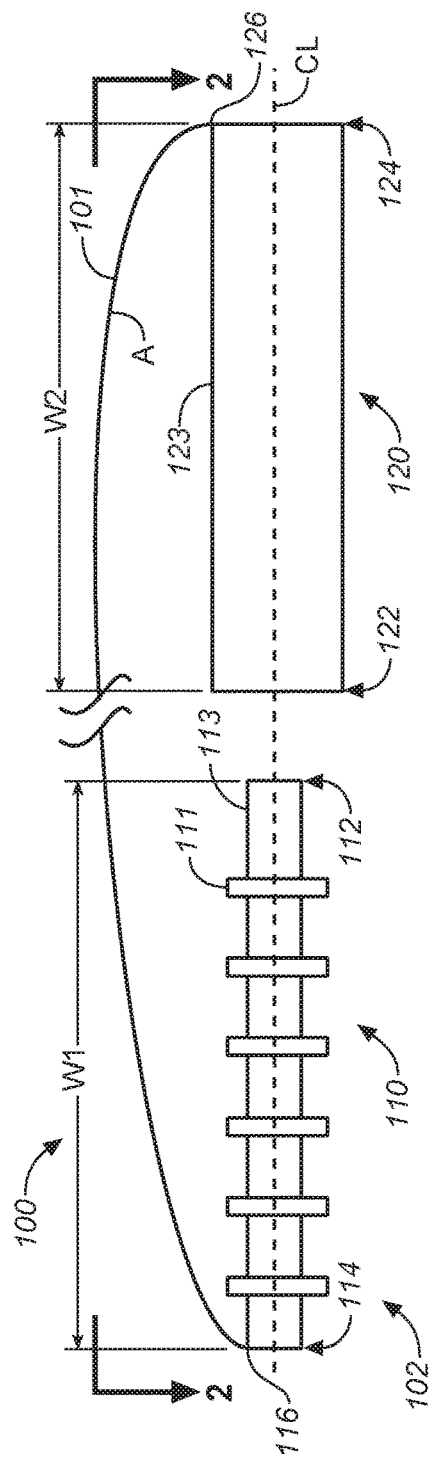
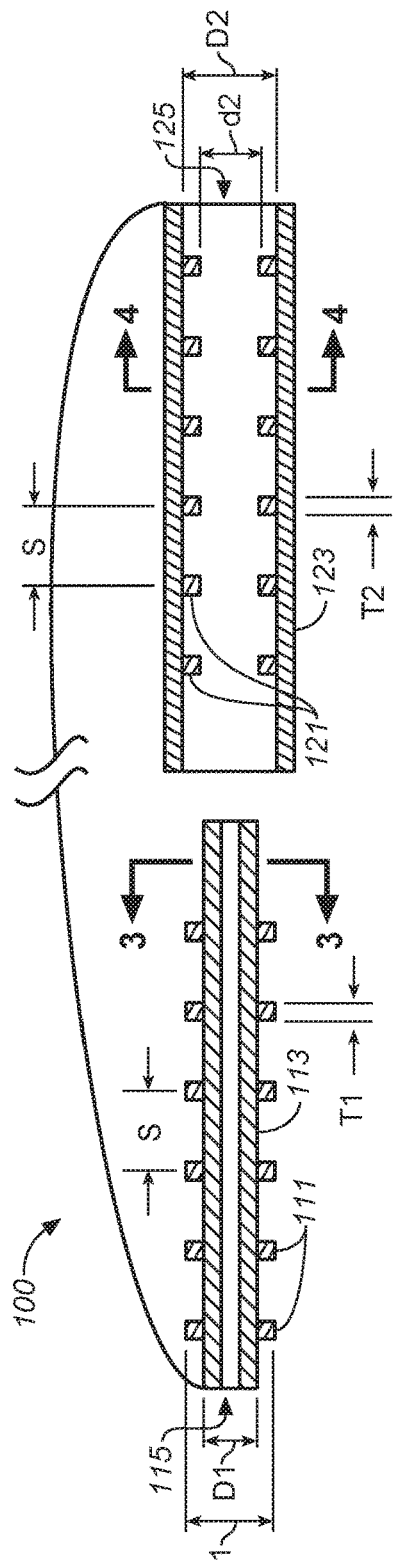
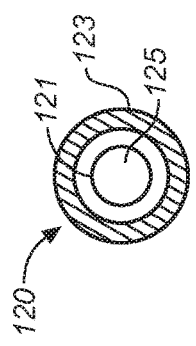

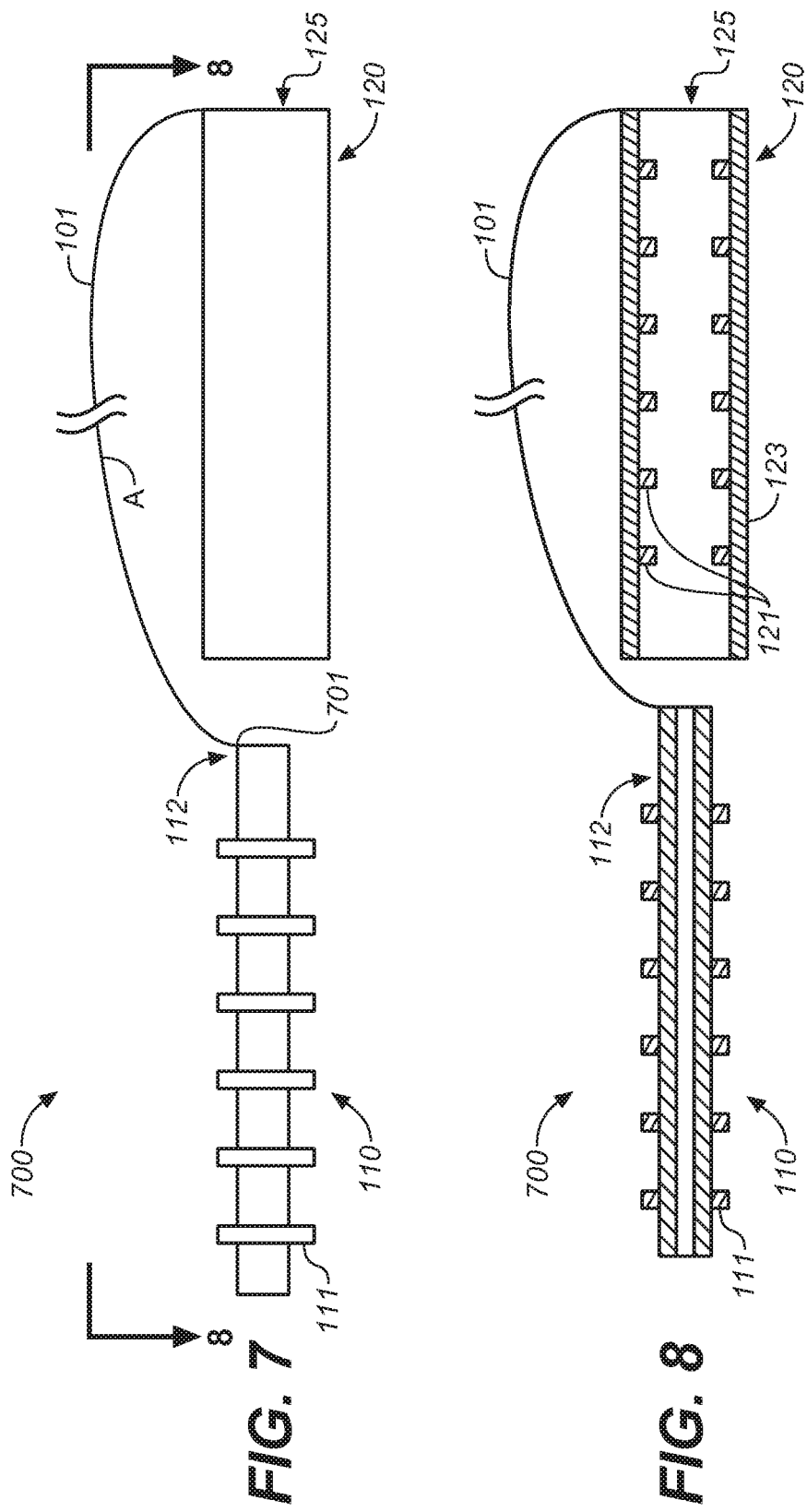

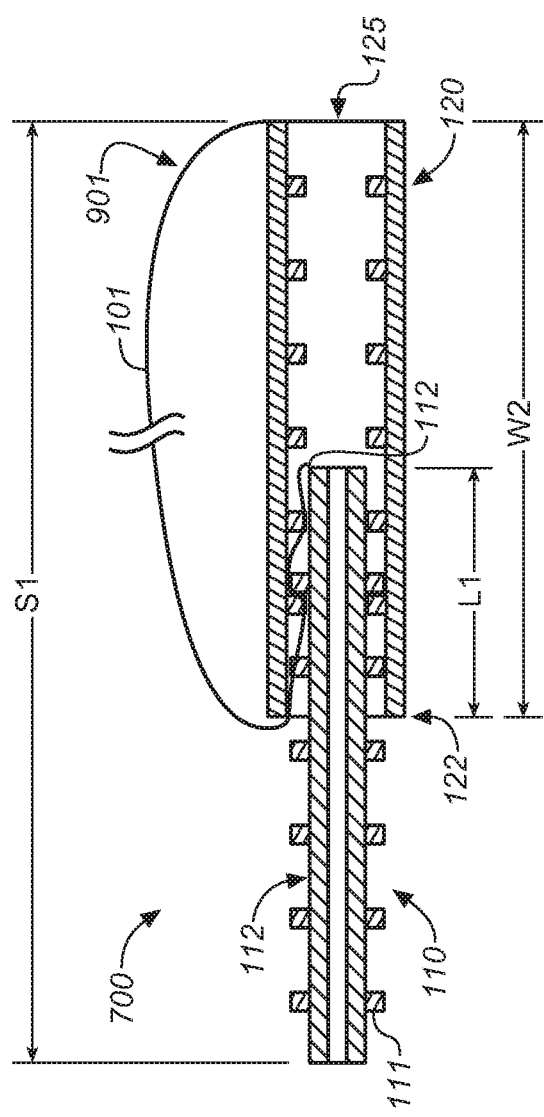
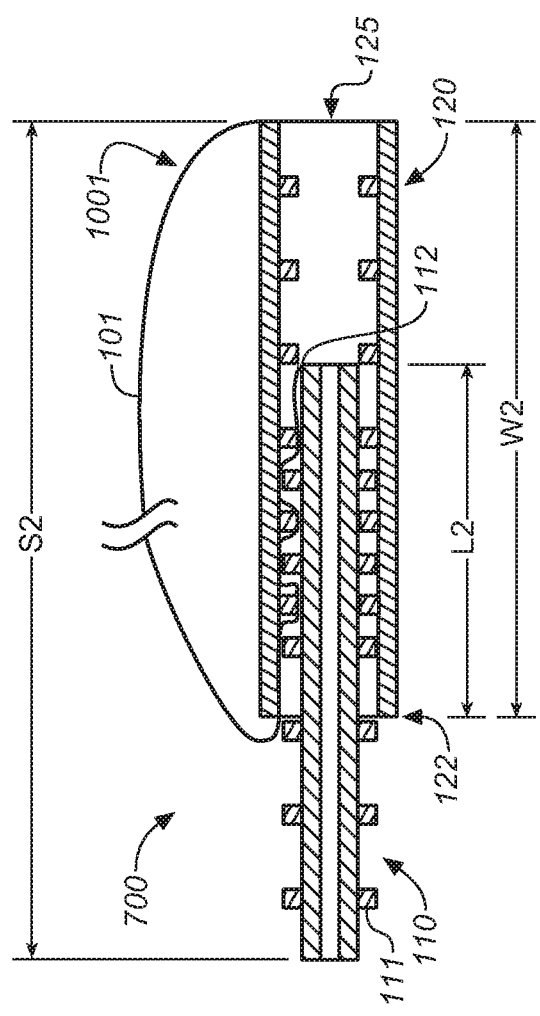

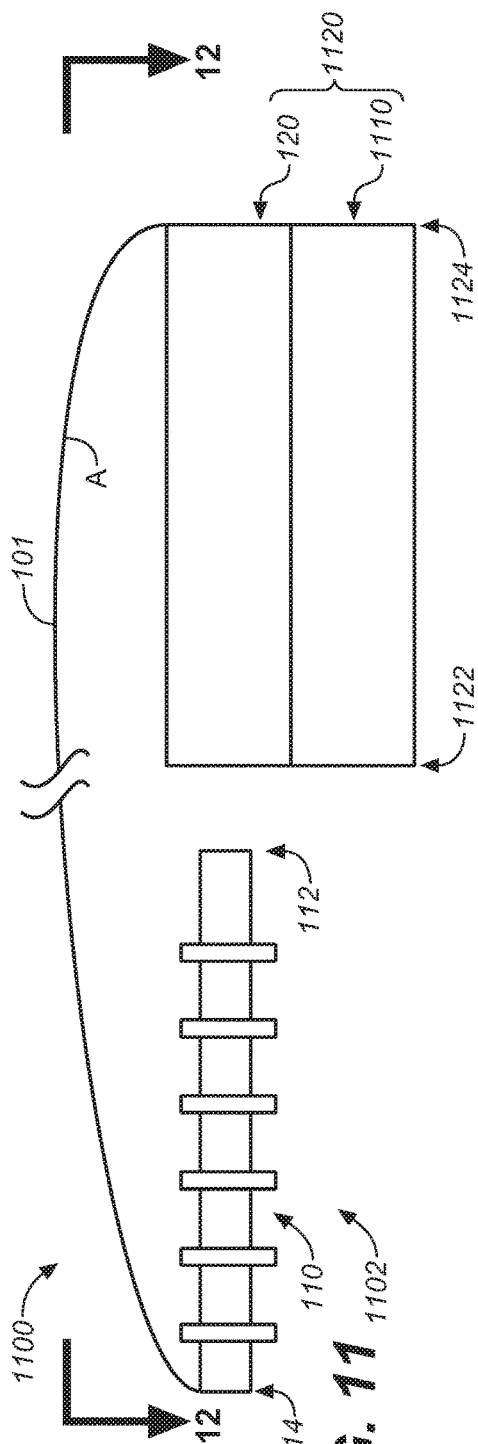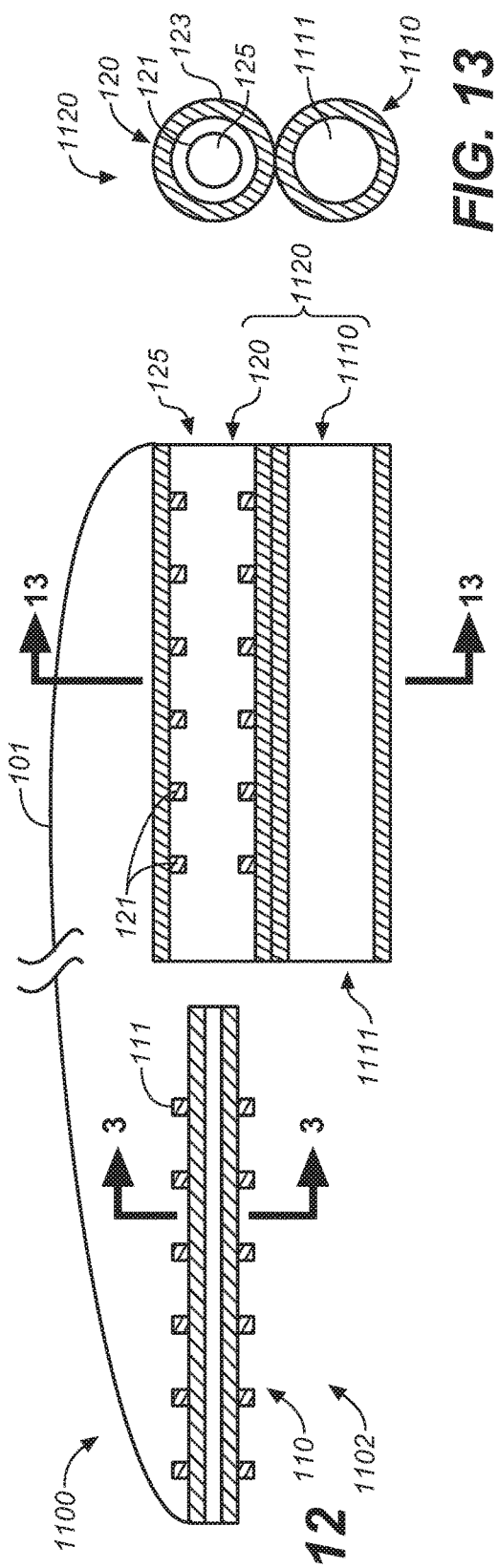

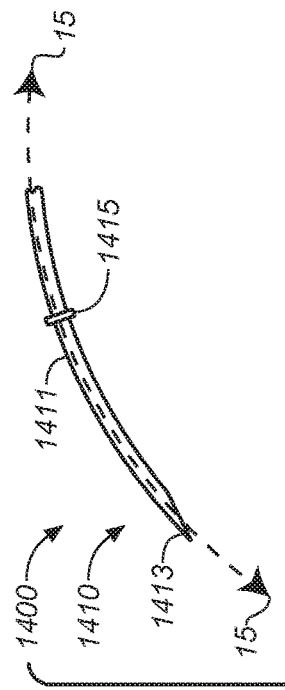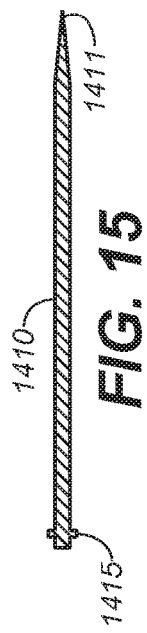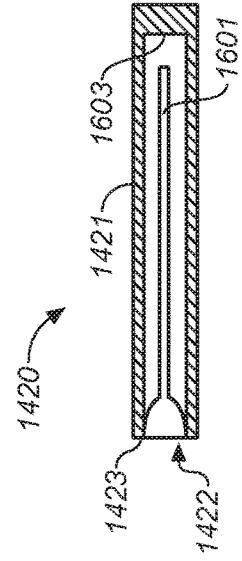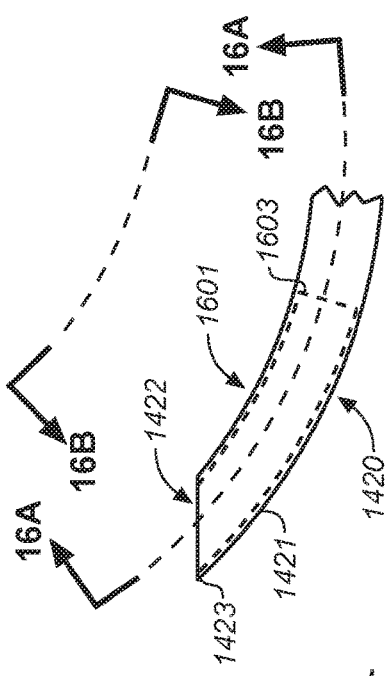

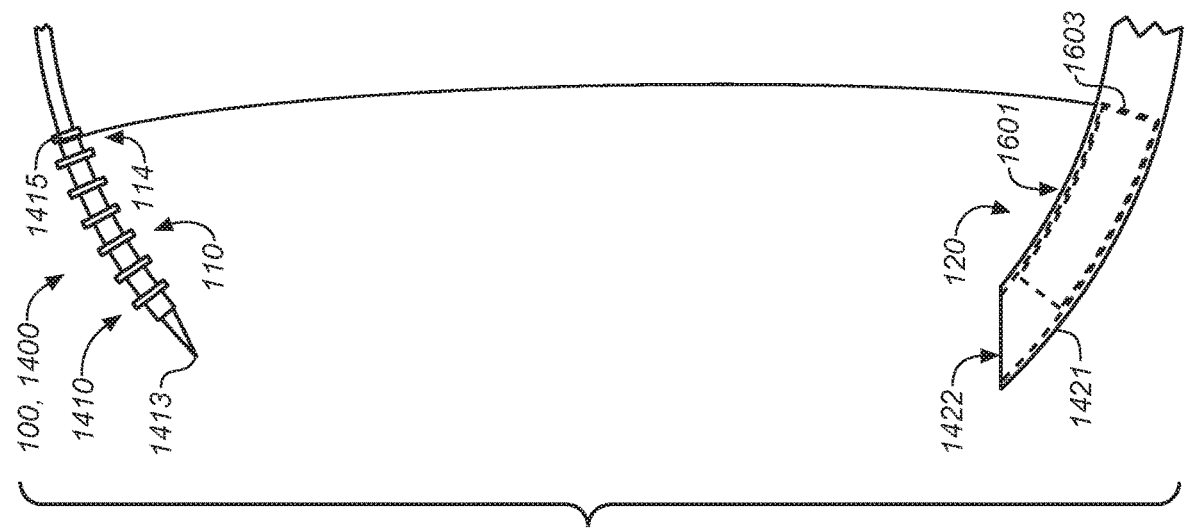
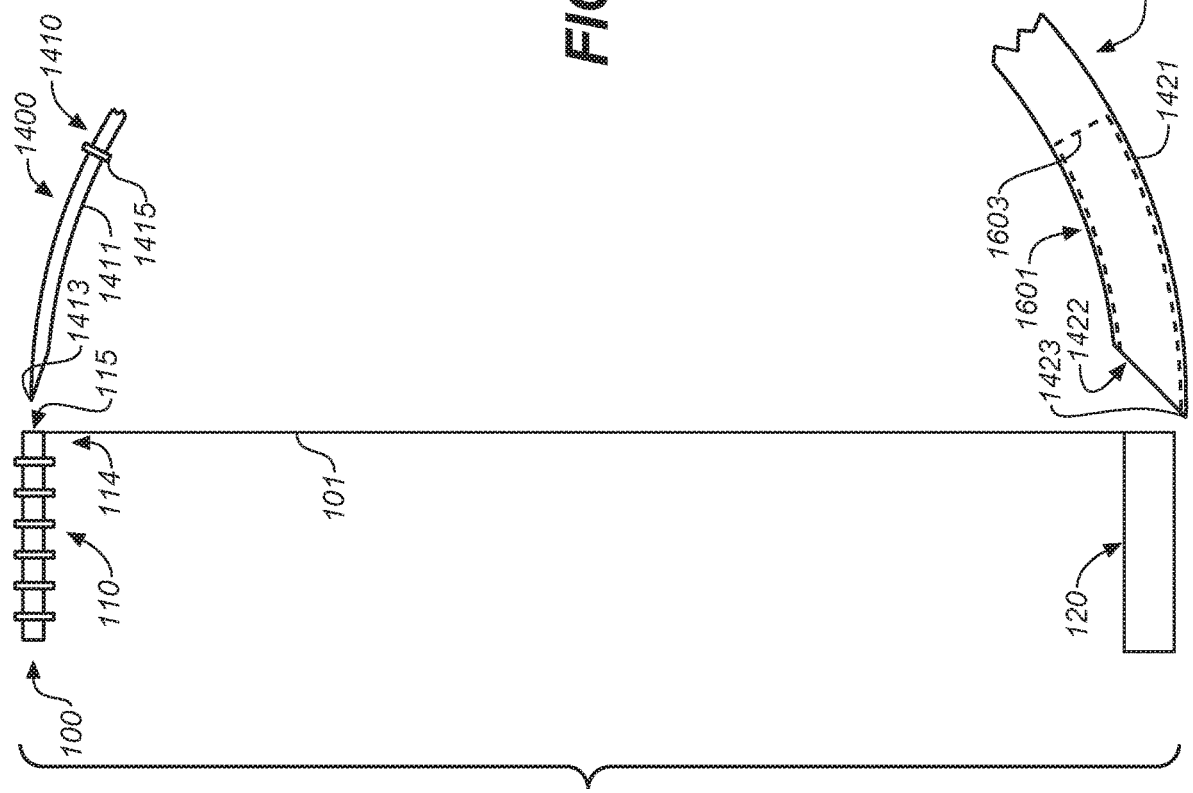

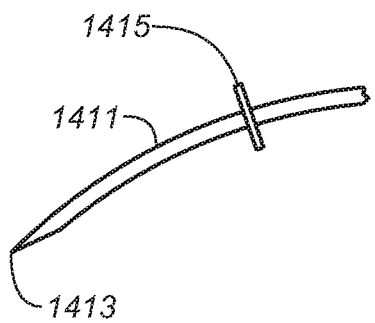
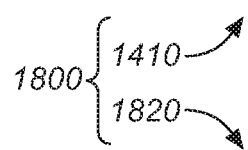
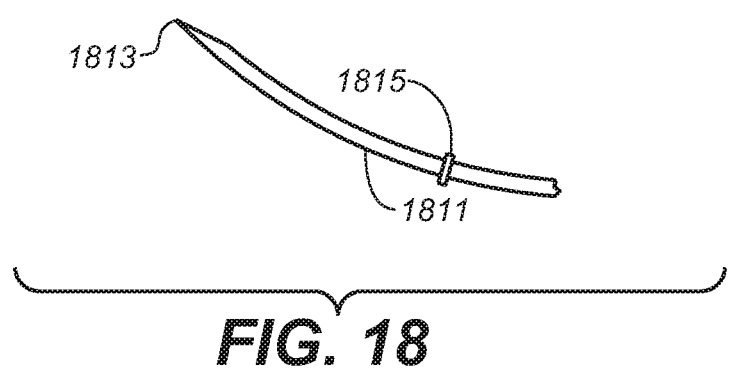
FIG. 18

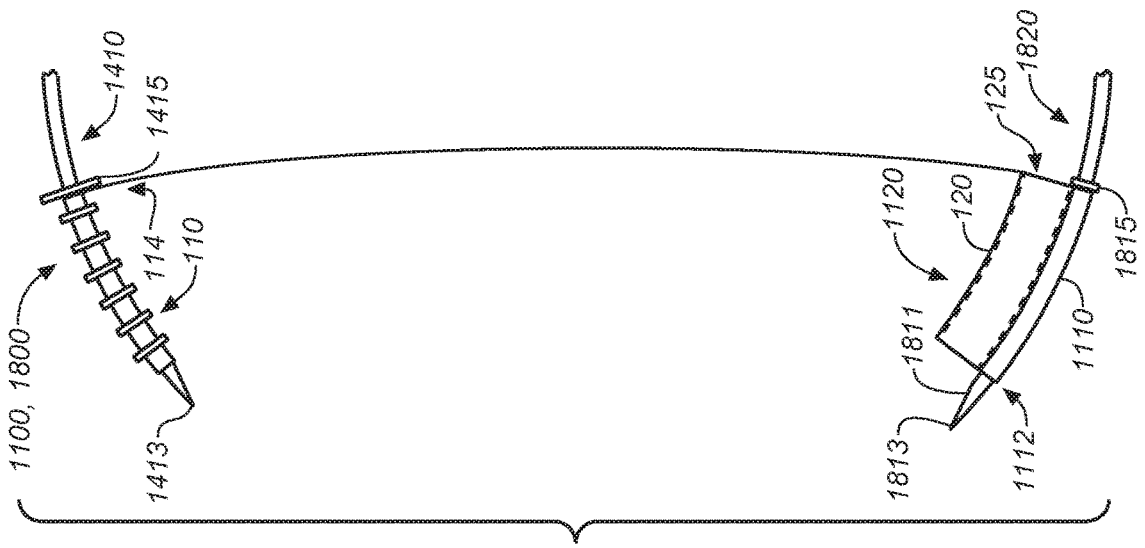
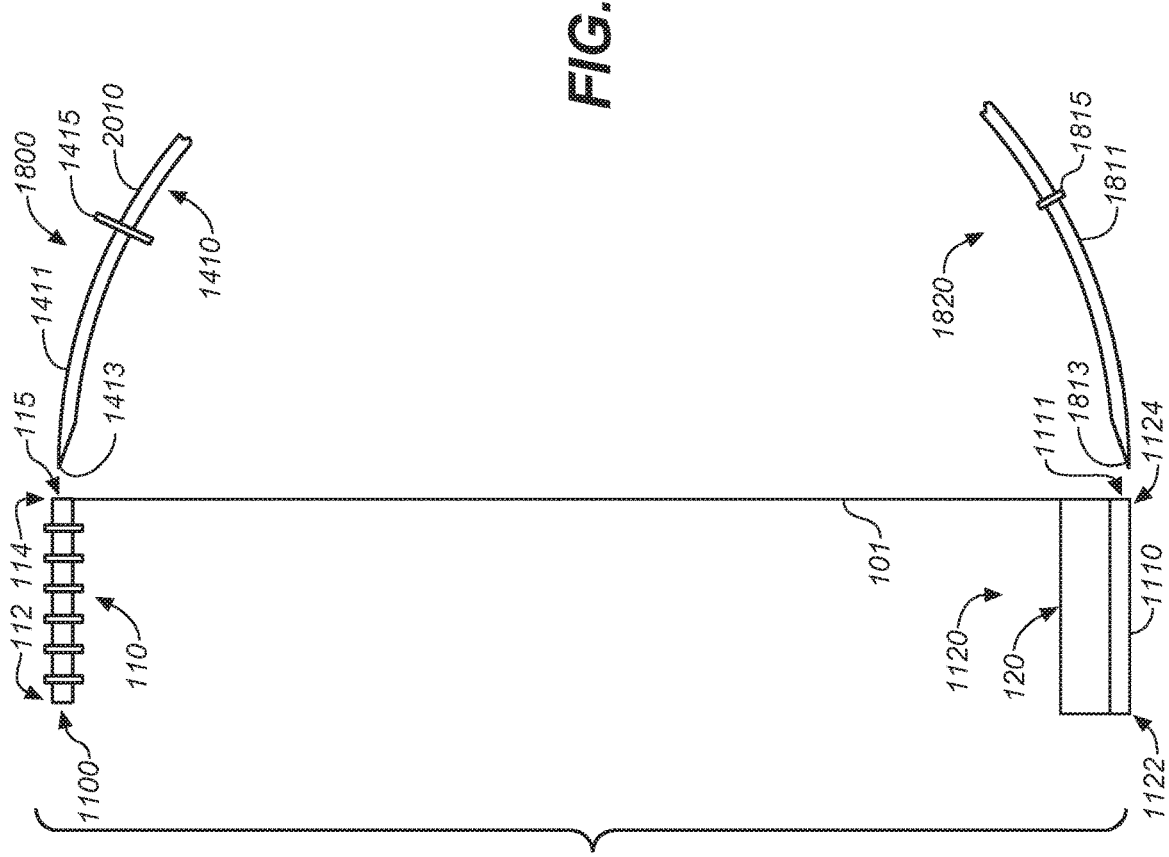

SURGICAL SUTURE AND METHOD OF SUTURING

CROSS-REFERENCE TO RELATED APPLICATIONS

This application claims the benefit of U.S. Provisional Application No. 62/585,471, filed Nov. 13, 2017, U.S. Provisional Application No. 62/599,430, filed Dec. 15, 2017, U.S. Provisional Application No. 62/633,373, filed Feb. 21, 2018, and U.S. Provisional Application No. 62/673,760, May 18, 2018, the contents of which are hereby incorporated by reference in their entirety.

BACKGROUND OF THE INVENTION

Field of the Invention

The present invention generally relates to surgical sutures and to methods of suturing, and more specifically to surgical suture including fastener elements and a method of using such surgical sutures.

Discussion of the Background

Suturing of body tissues has historically been performed by hand sewing over a continuous of a length of a wound. Studies demonstrate that interrupted sutures are preferred to continuous sutures; however, interrupted sutures, as performed by hand, are doubly time consuming. Techniques for interrupted suturing have been developed using surgical staples, which are typically delivered using a hand-held stapler.

While the use of surgical stapes is effective and fast, there are several problems with surgical staples, including difficulty of accessing remote sites in the body, lack of control of the size and/or tension on the staple, and malfunctions of the staplers, which can have serious medical complications.

There is a need for a surgical suture that is easy and inexpensive to manufacture, that allows the surgeon to accurately and easily close the suture to a desired size and/or to a desired tension, and that has a minimal number of parts. There is also a need for a method of applying such surgical sutures that is consistent with surgical techniques, that is easy to use, that is applicable to a variety of different types of surgeries.

BRIEF SUMMARY OF THE INVENTION

The present invention overcomes the disadvantages of prior art by providing a surgical suture consisting of of a pliable suture material with harder ends crafted to interdigitate, and therefore lock closed together, when pre-loaded onto specially designed needle device. The resulting closure has an adjustable tension, and, as a result of materials selected, can be either permanent or absorbable. The inventive surgical sutures can be used for closures intra-abdominally and intra-vascularly, for closure of fascia, closure of skin, and for closure of muscle It is one aspect to provide an apparatus including a surgical suture and a surgical suture holding device. The surgical suture includes a first fastener element including a first body having a proximal and a distal end, where the first body includes a first lumen and a first plurality of locking elements which protrude away from the first body, a second fastener element including a second body having a proximal and a distal end having a proximal and a distal end, where the second body includes a second lumen and a second plurality of locking elements within the second lumen, and a length of suture having a first end attached to the first fastener element and a second end attached to the second fastener element. The surgical suture holding device includes a first fastener element holding device including a first needle, where the first needle has a first tip, and where the first needle fits within the first lumen of the first fastener element, and a second fastener element holding device adapted to accept the second fastener element. With the first needle placed through the first lumen, and when the distal end of first fastener element is inserted into the distal end of the second lumen of the second fastener element, the first plurality of locking elements interact with the second plurality of locking elements to inhibit movement of the first fastener element from the second fastener element.

It is another aspect to provide an apparatus including a surgical suture and a surgical suture holding device: The a surgical suture includes a first fastener element having a proximal and a distal end, where the first fastener element includes a first body having a first lumen between the proximal end and the distal end, and a first plurality of locking elements disposed between the first proximal end and the first distal end and which protrude away from the first body, a second fastener element including a second body having a second lumen between a second proximal end and a second distal end, and a second plurality of locking elements disposed between the second proximal end and the second distal and within the second lumen, and a length of suture having a first end attached to the first fastener element and a second end attached to the second fastener element. The surgical suture holding device includes a first fastener element holding device including a first needle, where the first needle has a first tip, where the first needle is sized to accept the first lumen, and a second fastener element holding device adapted to accept the second fastener element. When the first needle placed through the first lumen, and when the distal end of the first fastener element is inserted into the distal end of the second lumen of the second fastener element, the first plurality of locking elements interact with the second plurality of locking elements to inhibit movement of the first fastener element from the second fastener element.

Yet another aspect is to provide a method of suturing. The method uses a surgical suture including a first fastener element including a first body having a first lumen extending from a first proximal end to a first distal end, and a first plurality of locking elements protruding away from the first body, a second fastener element including a second body having an outer surface and a second lumen extending from a second proximal end and a second distal end, and a second plurality of locking elements within the second lumen, and a length of suture having a first end attached to the first fastener element and a second end attached to the second fastener element. The method further uses a first fastener element holding device including a first needle sized to fit within the first lumen and a second fastener element holding device sized to hold the second fastener element. The method includes: inserting the first needle of the first fastener element holding device through the first lumen of the first fastener element; accepting the second fastener element in the second fastener element holding device; inserting the first needle of the first fastener element holding device into the body of a patient; moving the first fastener element holding device towards the second fastener element holding device, such that the first plurality of locking elements interact with the second plurality of locking elements to to inhibit movement of the first fastener element from the second fastener element; and removing the surgical suture from the first fastener element holding device and the second fastener element holding device.

These features together with the various ancillary provisions and features which will become apparent to those skilled in the art from the following detailed description, are attained by the surgical suture and method of suturing of the present invention, preferred embodiments thereof being shown with reference to the accompanying drawings, by way of example only, wherein:

BRIEF DESCRIPTION OF THE SEVERAL VIEWS OF THE DRAWING

FIG. 1 side view of a first embodiment device including a suture and a pair of fastener elements;

FIG. 2 is a sectional view 2-2 of FIG. 1;

FIG. 3 is a sectional view 3-3 of FIG. 2;

FIG. 4 is a sectional view 4-4 of FIG. 2;

FIG. 7 side view of a second embodiment device including a suture and a pair of fastener elements;

FIG. 8 is a sectional view 8-8 of FIG. 7;

FIG. 9 is a sectional view 8-8, showing a first configuration of the pair of fastener elements;

FIG. 10 is a sectional view 8-8, showing a second configuration of the pair of fastener elements;

FIG. 11 side view of a third embodiment device including a suture and a pair of fastener elements;

FIG. 12 is a sectional view 12-12 of FIG. 11;

FIG. 13 is a sectional view 13-13 of FIG. 12;

FIG. 14 is a top view of first embodiment pair of fastener element holding devices for use with the surgical suture of FIG. 1;

FIG. 15 is a sectional view 15-15 of FIG. 14;

FIG. 16A is a sectional view 16A-16a of FIG. 14;

FIG. 16B is a side view 16B-16B of FIG. 14;

FIGS. 17A, 17B, 17C, and 17D are sequential top views of the use of the pair of fastener element holding devices of FIG. 14 for securing a surgical suture of FIG. 1;

FIG. 18 is a top view of a second embodiment pair of fastener element holding devices for use with the surgical suture of FIG. 11;

FIGS. 19A, 19B, 19C, and 19D are sequential top views of the use of the fastener element holding devices of FIG. 18 for delivering a surgical suture of FIG. 11.

Figure 5:
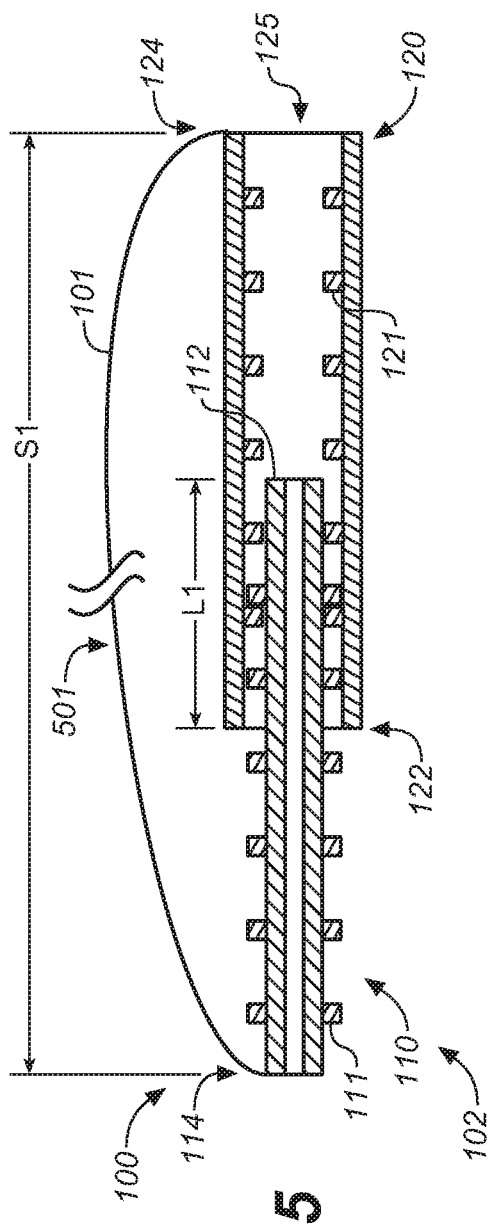
FIG. 5 is a sectional view 2-2, showing a first configuration of the pair of fastener elements.

Reference symbols are used in the Figures to indicate certain components, aspects or features shown therein, with reference symbols common to more than one Figure indicating like components, aspects or features shown therein.

DETAILED DESCRIPTION OF THE INVENTION

Various embodiments are described herein as a surgical suture and methods for suturing. The surgical suture may include a device that includes a pair of matching fastener elements and a length of suture joining the fastener elements. Surgeons may use the inventive surgical suture to close wounds, which may include but are not limited to, suturing a subfascial, a fascial, or intra-arterial wound. In certain embodiments, one or both of the fastener elements are configured to be manipulated by needles. When the needles are then moved to approach each other, the pair of fastener elements interlock. When the needles are removed from the fastener elements, the remaining locked fastener elements and connecting suture close the wound.

FIG. 1 side view of a first embodiment surgical suture 100, which includes a length, A, of suture 101 and a pair of cooperating fastener elements 102, and which further includes a first fastener element 110 and a second fastener element 120, FIG. 2 is a sectional view 2-2 of FIG. 1, FIG. 3 is a sectional view 3-3 of FIG. 2 of the first fastener element, and FIG. 4 is a sectional view 4-4 of FIG. 2 of the second fastener element.

First fastener element 110 includes a body 113 having an outer diameter D1 and a lumen 115 that extends a length W1 from a proximal end 114 of the body to a distal end 112 of the body. First fastener element 110 also includes a plurality of locking elements 111, with spacing S, disposed along the outer surface of body 113, each having a longitudinal width T1, and which extends from diameter D1 to a diameter d1.

Second fastener element 120 includes a body 123 having a lumen 125 with an inner diameter D2 that extends a length W2 from a proximal end 124 of the body to a distal end 122 of the body. Second fastener element 120 also includes and a plurality of locking elements 121 disposed along the inside of lumen 125, with the same spacing S as locking elements 111, and which extend from diameter D2 to a diameter d2 and have a longitudinal width T2.

Suture 101 connects the pair of fastener elements 120 at proximal ends 114 and 124. Suture 101 may, but is not limited, to being formed from an absorbable suture material, such as DEXON™ or MAXON™ (both manufactured by Covidien AG, Neuhausen am Rheinfall, Switzerland) or a non-absorbable suture material, such as prolene (manufactured by Ethicon, Somerville, N.J.), and the fastener elements may be formed from thicker or a hardened version of either an absorbable or non-absorbable suture material.

Suture 100 and the pair of fastener elements 102 are sized for the type of fastener being performed. In various embodiment, for example, the fastener element is sized to fit over a needle having a size of 40, 50, 30, 0, 1 that may be, for example and without limitation, 7 mm long. In certain embodiments, the length of the fastener element is less than the length of the needle, and for a 7 mm long needle may be 5 mm long, and the suture may have a length of from 5-7 mm. The use of other sized fastener elements, suture lengths, and needle sizes would, in light of this disclosure, be obvious to one skilled in the art.

The embodiments described herein may be used to close a variety of sizes of wounds and/or incisions using suitably sized suture devices, as would be apparent to one skilled in the art.

Figure 6:
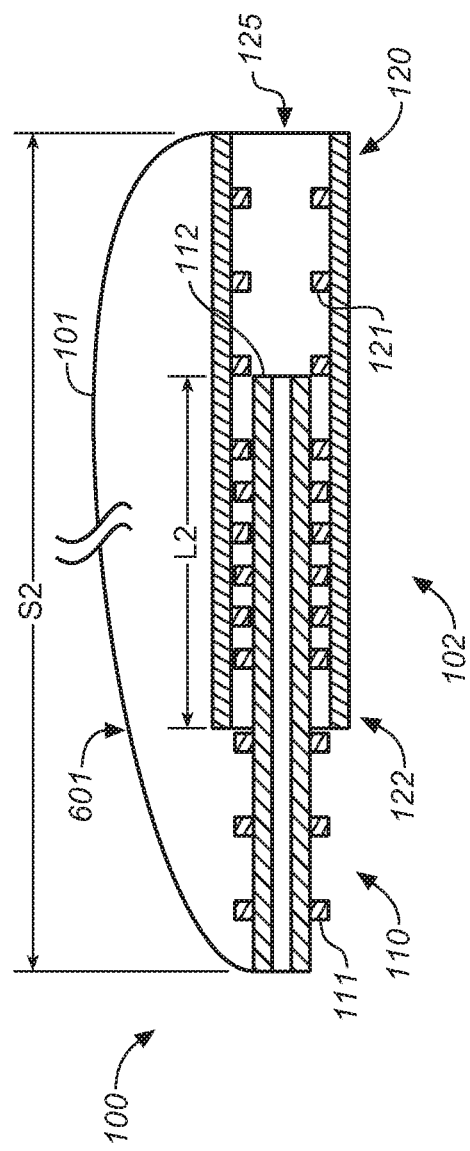
FIG. 6 is a sectional view 2-2, showing a second configuration of the pair of fastener elements.

In general, suturing with surgical suture 100 may include inserting distal end 112 of first fastener element 110 into distal end 122 of lumen 125 of second fastener element 120, as illustrated in FIGS. 5 and 6, where FIG. 5 is a sectional view 2-2 of FIG. 1, showing a first configuration of surgical suture 100 and the resulting loop 501, and FIG. 6 is a sectional view 2-2, showing a second configuration of surgical suture 100 and the resulting loop 601.

Thus, for example, FIG. 5 illustrates a configuration where fastener elements 102 overlap, or are engaged, by a distance of L1. More specifically, distal end 112 extends a distance L1 into element 124, which results in a distance S1 between proximal ends 114 and 124, where S1=W1+W2−L1. In this configuration, the length of loop 501 includes the length of suture 101, A, plus the distance S1.

FIG. 6 illustrates another configuration, where the overlap of fastener elements 102 is a distance L2, which is greater than the distance L1. More specifically, distal end 112 extends a distance L2 into element 124, which results in a distance S2 between proximal ends 114 and 124, where S2=W1+W2−L2. In this configuration, the length of loop 601 includes the length of suture 101, A, plus the distance S2.

FIGS. 5 and 6 thus illustrate that the length of the suture loop is adjustable, to within the spacing S, according to how far the fastener elements 102 overlap. As described subsequently, these loops may be surgically placed with the body to hold tissue within the loop.

In certain embodiments, the dimensions D1, d1, D2, and d2 are sized so that locking elements 111 and 123 interact when first fastener element 110 is inserted into second fastener element 120. Thus, for example, locking elements 111 extend from the centerline of first fastener element 110 from D1/2 to d1/2, while locking elements 113 extend from the centerline of second fastener element 120 from d2/2 to D2/2. In certain embodiments there is radial overlap of locking elements 111 and 113. Thus, for example, if d2=D1 and D2=d1, then each one of locking element 111 and 113 will attempt to occupy the same space as they engage. Locking elements 111 and 113 are preferably flexible, allowing them to bend as first fastener elements 110 is inserted into fastener element 120. The amount of force required to engage fastener elements 110 and 120 depends on the actual dimensions of d1, D1, d2, and D2, as well as the longitudinal widths w1 and w2 and the actual shape of each locking element 111 and 113, and the materials used. It is within the knowledge of one skilled in the art to design locking elements 111 and 113 for a desired force for pushing fastener elements 110 and 120 together, and for pulling fastener elements 110 and 120 apart.

In certain other embodiments, one or both of locking elements 111 and 121 are flexible, allowing the equally spaced locking elements to engage at each spacing S. In certain embodiments, the shapes of locking elements 111 and 121 are shaped to make it more difficult to pull the fastener elements apart, effectively allowing the surgeon to ratchet as the locking elements 111 and 123 engage with each other.

In various alternative embodiments, the diameters d1, D1, d2, and/or D2 vary along the length of the first and/or second fastener element, and/or fastener elements 110 and 120 may be curved, and not straight, as shown in the Figures.

FIG. 7 side view of a second embodiment surgical suture 700, and FIG. 8 is a sectional view 8-8 of FIG. 7. Surgical suture 700 is generally similar to surgical suture 100, except as explicitly stated.

Surgical suture 700 includes suture 101 and the pair of fastener elements 102, shown as first fastener element 110 and a second fastener element 120. Suture 101 is attached to distal end 112 of the first fastener element 110 and proximal end 124 of second fastener element 120, which is different from the suture attachment of surgical suture 100. The main effect of the suture placements is that for similarly sized elements and overlap of fastener elements, part of the suture is located in the overlap of the fastener elements, resulting in a smaller loop.

In general, suturing with surgical suture 700 is similar to suturing using surgical suture 100, as illustrated in FIGS. 9 and 10, where FIG. 9 is a sectional view 8-8 of FIG. 7, showing a first configuration of surgical suture 700 resulting in a loop 901, and FIG. 10 is a sectional view 8-8, showing a second configuration of the pair of fastener elements and resulting in a loop 1001.

Thus, for example, FIG. 9 illustrates a configuration where fastener elements 102 overlap by a distance of L1. More specifically, distal end 112 is positioned to extends a distance L1 within element 124, which results in a distance S1 between proximal ends 114 and 124, where S1=W1+W2−L1, as in FIG. 5. Given the position of suture 101 on fastener elements 102, a length L1 of the suture is held between the fastener elements and does not contribute to the length of loop 901. Surgical suture 700 thus forms a loop 501 which includes the length of suture 101, A, minus the length L1, plus the length W2.

FIG. 10 illustrates another configuration, where the overlap of fastener elements 102 is a distance L2. Surgical suture 700 thus forms a loop 1001 which is the length of suture 101, A, minus the length L2, plus the length W2.

FIGS. 9 and 10 thus illustrate that the length of the loop is adjustable, and the length of the loop is generally less than that of surgical suture 100

FIG. 11 side view of a third embodiment surgical suture 1100, FIG. 12 is a sectional view 12-12 of FIG. 11, and FIG. 13 is a sectional view 13-13 of FIG. 12. Surgical suture 700 is generally similar to surgical suture 100 or 700, except as explicitly stated.

Surgical suture 1100 includes suture 101 and a pair of fastener elements 1102, which includes first fastener element 110 and a third fastener element 1120. Third fastener element 1120 has a distal end 1122 and a proximal end 1124, and is formed from second fastener element 120 and a tubular member, or tube 1110, having a lumen 1111, and which is attached to the second fastener element. Suture 101 is attached to proximal end 114 of first fastener element 1120 and to proximal end 1124 of second fastener element 1120. In an alternative embodiment, suture 101 is attached to distal end 112 of first fastener element 1120 and to proximal end 1124 of second fastener element 1120.

FIG. 14 is a top view of a first embodiment pair of fastener element holding devices 1400 for use with surgical suture 100, FIG. 15 is a sectional view 15-15 of FIG. 14, and FIG. 16 is a sectional view 16-16 of FIG. 14. Pair of embodiment fastener element holding devices 1400 includes a first fastener element holding device 1410 and a second fastener element holding device 1420. First fastener element holding device 1410 includes a needle 1411 having a tip 1413 at a distal end and a stop 1415 distally located. Second fastener element holding device 1420 includes a body 1421, which has a lumen 1422 that extends from a tip 1423 at a distal end at a stop 1603, and a slot 1611 through the side of the lumen.

Stops 1415 and/or 1603 are, in general, configurations of elements locate the fastener elements within the fastener element holding devices, and may include any combination of variation is diameters (such as needles and lumens), or additional elements which prevent the fastener elements from moving unimpeded in a proximal direction in a fastener element holding device.

The fastener element holding devices may include needles having a size of 40, 50, 30, 0, 1 for placing through lumens of a fastener element, or may be larger to contain a fastener element within the lumen. The surgical suture handing devices are formed from stainless steel.

Figure 17C:
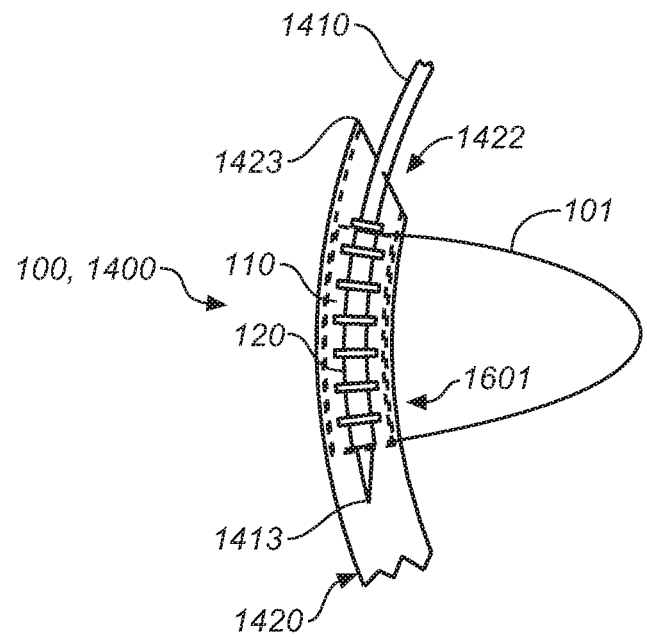

FIGS. 17A, 17B, 17C, and 17D are sequential top views of the use of the pair of fastener element holding devices 1400 for securing surgical suture 100. As shown in FIG. 17A, first fastener element holding device 1410 may be used with first fastener element 110 and second fastener element holding device 1420 may be used with second fastener element 120. Specifically needle 1411 is sized to fit through lumen 115 of first fastener element 110, and lumen 1422 is sized to accept second fastener element 120 within body 1421.

FIG. 17B shows that tip 1413 of needle 1411 is placed into the end of lumen 115 of first fastener element 110 at proximal end 114, until the proximal end of the first fastener element rests against stop 1415, with the needle protruding thought distal end 112. Further, proximal end 124 of second fastener element 120 is inserted into lumen 1422 until the element rests on stop 1603. Second fastener element 120 fits fully within fastener element holding device 1420. In certain embodiments, suture 101, which connects fastener element 110/120, is placed through slot 1601. In certain embodiments, second fastener element 120 is provided to a surgeon preloaded into lumen 1422, and in an alternative embodiment, the open end of lumen 1422 is covered with a layer of a plastic, which is punctured by needle 1413 during suturing.

As illustrated in FIG. 17C, fastener element holding devices 1410/1420 are aligned so that tip 1413 passes through tip 1423 and into lumen 1422, with first fastener element 110 being inserted into lumen 125 of second fastener element 120. At this point, fastener elements 110 and 120 are engaging, as shown, for example, in FIG. 5 or 6, according to how far first fastener element holding device 1410 is inserted into lumen 1422 of second fastener element holding device 1420.

Figure 17D:
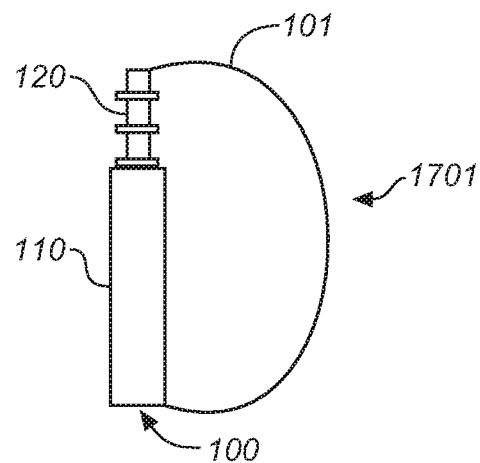

FIG. 17D shows the configuration of surgical suture 100 after fastener elements 110 and 120 are removed from fastener element holding devices 1410/1420 and forming a loop 1701.

FIG. 18 is a top view of a second embodiment pair of fastener element holding devices 1800 for use with surgical suture 1100. The pair of fastener element holding devices 1800 is generally similar to fastener element holding devices 1400, except as explicitly stated.

The pair of fastener element holding devices 1800 includes first fastener element holding device 1410 and a third first fastener element holding device 1820. Third first fastener element holding device 1820 is generally similar to first fastener element holding device 1410, and includes a needle 1811 having a tip 1813 and a stop 1815.

Figure 19C:
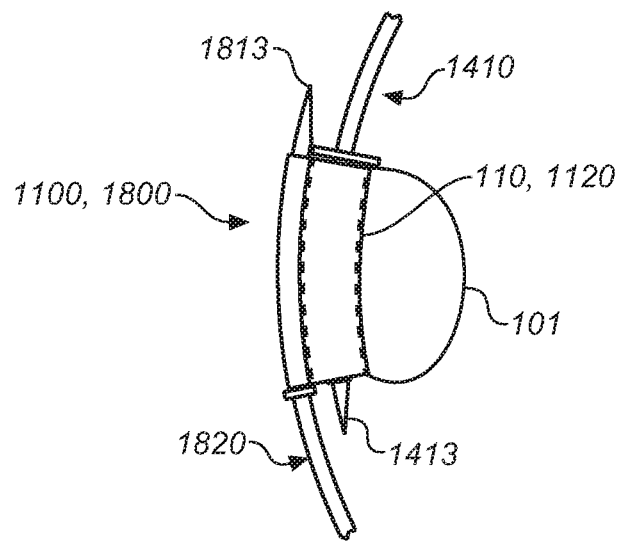

FIGS. 19A, 19B, 19C, and 19D are sequential top views of the pair of fastener element holding devices 1800 for delivering surgical suture 1100. As shown in FIG. 19A, first fastener element holding device 1410 may be used with first fastener element 110 and third fastener element holding device 1820 may be used with second fastener element 1120. Specifically needle 1411 is sized to fit through lumen 115 of first fastener element 110, and needle 1811 is sized to fit through lumen 1111 of third fastener element 1120. Thus, needle 1411 and 1811 are generally the same and have sizes matching the size of the lumen through which they are to be inserted.

FIG. 19B shows that tip 1413 of needle 1411 is placed into the end of lumen 115 of first fastener element 110 at proximal end 114, until the proximal end of the first fastener element rests against stop 1415, with the needle protruding thought distal end 112. Further, tip 1813 of needle 1811 is placed into the end of lumen 1111 of third fastener element 1120 at proximal end 1124, until the proximal end of the third fastener element rests against stop 1815, with the needle protruding thought distal end 1122.

As illustrated in FIG. 19C, fastener element holding devices 1410/1820 are aligned so that tip 1413 passes through lumen 125 of third fastener element 1120. At this point, fastener elements 110 and 120 are engaging, as shown, for example, in FIG. 5 or 6.

Figure 19D:
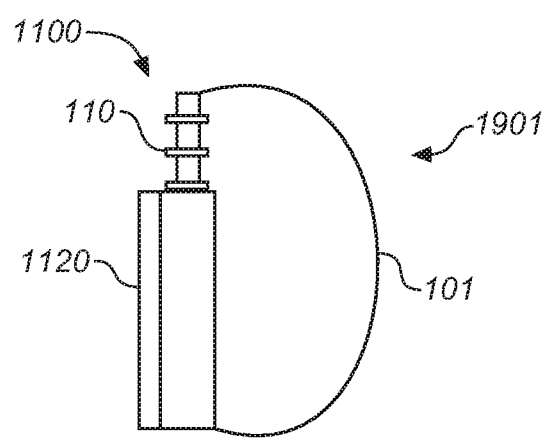

FIG. 19D shows the configuration of surgical suture 1100 after fastener elements 110 and 1820 are removed from fastener element holding devices 1410/1420 and forming a loop 1901.

FIGS. 20A, 20B, 20C, 20D, and 20E are sequential views of the use of the fastener element holding devices of FIG. 18 for delivering a surgical suture of FIG. 11 for suturing a wound.

Figure 20A:
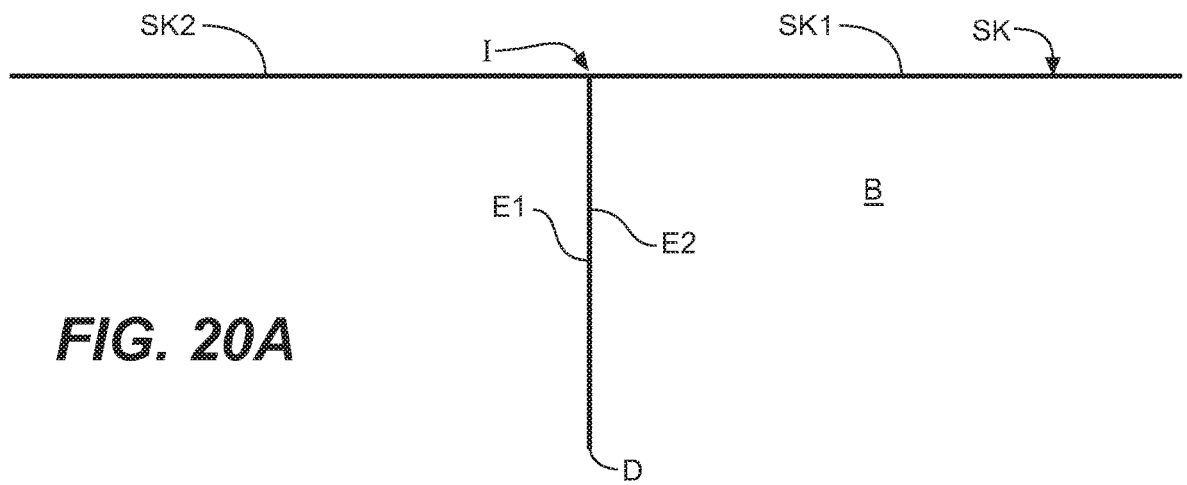
FIGS. 20A, 20B, 20C, 20D, and 20E are sequential views of the use of the fastener element holding devices of FIG. 18 for delivering a surgical suture of FIG. 11 for suturing a wound.

FIG. 20A is a schematic of a body B having a skin SK. A wound has made an incision I to a point D in the body, forming a first edge E1 and a second edge E2, and dividing skin SK into a first skin portion SK1 and a second skin portion SK2.

Figure 20B:
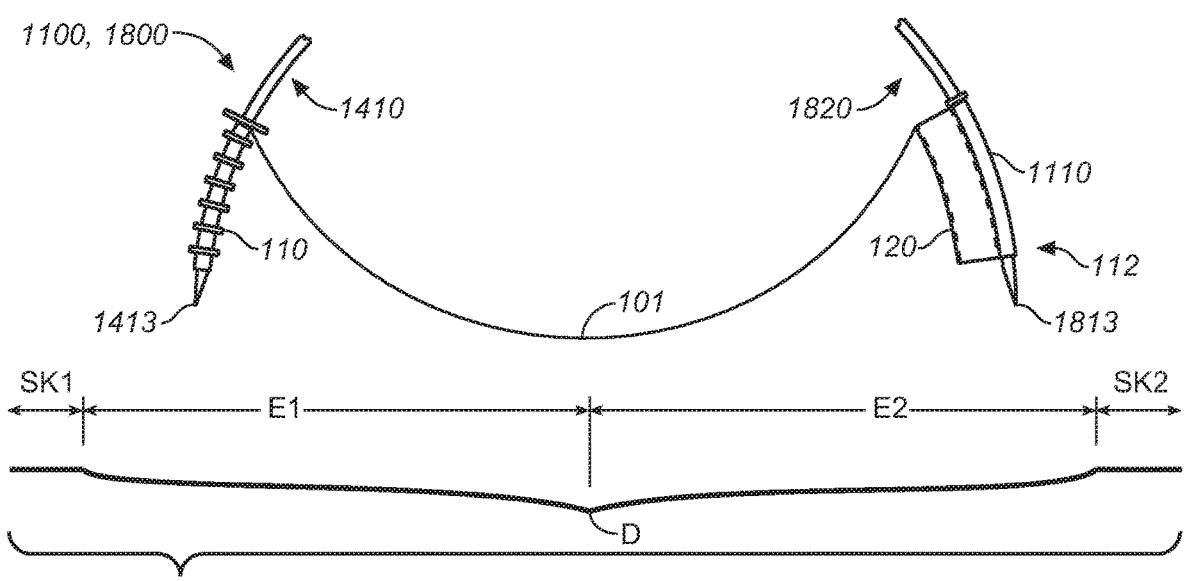
Figure 20C:
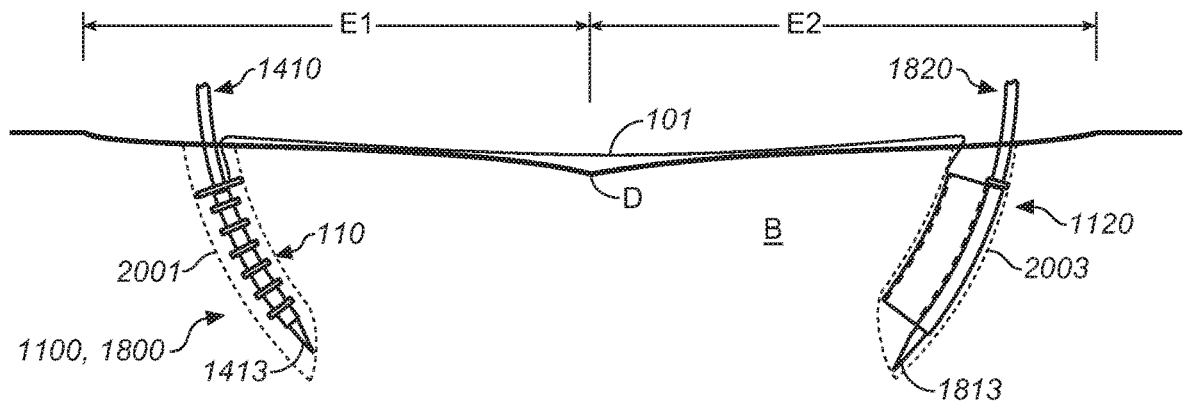

FIG. 20B shows that the incision I has been opened, exposing edges E1 and E2. The sequence of motions described in FIGS. 19A-D are now performed on body B. Tip 1413 of first fastener element holding device 1410 is positioned over edge E1, and tip 1813 of third fastener element holding device 1820 is positioned over edge E1. As fastener element holding devices 1410 and 1820 are threaded through body B, first fastener element holding device 1410 produces a hole 2001 in the body, and third fastener element holding device 1820 produces a hole 2003 through the body. Suture 100 remains outside of the body, along edges E1 and E2.

Figure 20D:
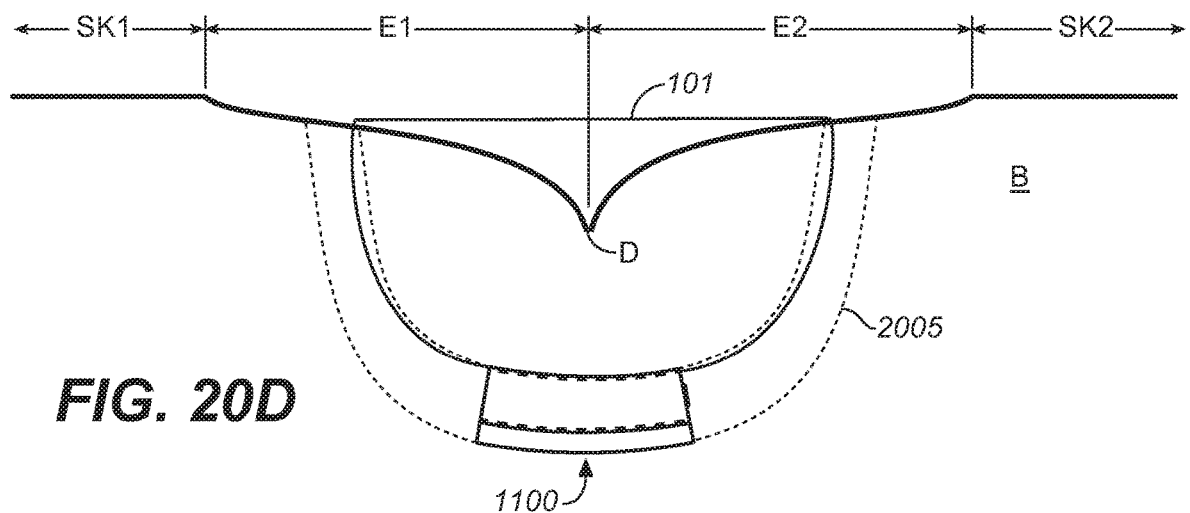
Figure 20E:
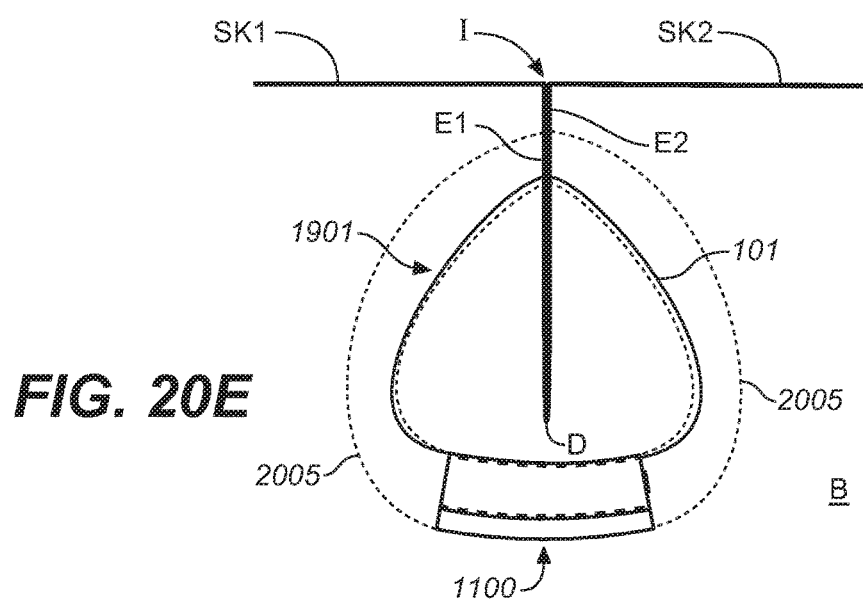

In FIG. 20D, fastener element holding devices 1410 and 1820 been removed, leaving a hole 2005 in body B. In FIG. 20E, skin SK has been relaxed, with edges E1 and E2 mating, and with surgical suture 1100 left in the body to hold the body together.

While FIG. 20 illusrates the method of suturing using surgical suture 1110 and fastener element holding devices 1410 and 1820, it will be apparrent to those skilled in the art that the other sutures and holding devices shown herein may be used using the same method for suturing.

Further, while the above example has been provided for performing a subcutaneous stitch, it will be obvious to those skilled in the art, that the devices may be used where hand suturing or stapling is used, including, but not limited to suturing a subfascial, a fascial, or intra-arterial wound.

In one alternative embodiment, a first fastener element is placed outside of the body, near the skin for example, and the second fastener element is held by a needle, which is threaded into the the body and back out, where it connects with the first fastener element.

Moreover, the fastener element holding devices described herein, and variations thereof, may be provided for delivery similar to hand-held surgical suture devices, described for example and without limitation is U.S. Pat. No. 5,258,010, incorporated herein by reference, or may provide for remote access to tissues, such as, without limitation, via robotic surgery, laparoscopic surgery, or intravascular delivery systems, as is known in the field.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment. Furthermore, the particular features, structures or characteristics may be combined in any suitable manner, as would be apparent to one of ordinary skill in the art from this disclosure, in one or more embodiments.

Similarly, it should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

I claim:

1. An apparatus comprising:
    a surgical suture including
    a first fastener element including a first body having a proximal and a distal end, where said first body includes a first lumen and a first plurality of locking elements which protrude away from said first body,
    a second fastener element including a second body having a proximal and a distal end, where said second body includes a second lumen and a second plurality of locking elements within said second lumen, and
    a length of suture having a first end attached to said first fastener element and a second end attached to said second fastener element; and
    a surgical suture holding device including
    a first fastener element holding device including a first needle, where said first needle has a first tip, and where said first needle fits within said first lumen of said first fastener element, and
    a second fastener element holding device adapted to accept said second fastener element,
    where, with said first needle placed through said first lumen, and when said distal end of first fastener element is inserted into the distal end of said second lumen of said second fastener element, said first plurality of locking elements interact with said second plurality of locking elements to inhibit movement of said first fastener element from said second fastener element.

2. The apparatus of claim 1, where said first fastener element holding device is configured to locate said first fastener element at a specific location in said first fastener element holding device.

3. The apparatus of claim 1, where said second fastener element holding device is configured to locate said second fastener element at a specific location in said second fastener element holding device.

4. The apparatus of claim 1, where said first plurality of locking elements are equally spaced along said first body, where said second plurality of locking elements are equally spaced along an inner surface of said second lumen with the same spacing as said first plurality of locking elements.

5. The apparatus of claim 1, where said first end of said suture is attached to either said proximal end of said first fastener element or said distal end of said first fastener element, and where said second end of said suture is attached to either said proximal end of said second fastener element or said distal end of said second fastener element.

6. The apparatus of claim 5, where said first end of said suture is attached to said proximal end of said first fastener element and where said second end of said suture is attached to said proximal end of said second fastener element.

7. The apparatus of claim 5, where said first end of said suture is attached to said distal end of said first fastener element and where said second end of said suture is attached to said proximal end of said second fastener element.

8. The apparatus of claim 1, where said second fastener element holding device includes a second needle having a third lumen adapted to accept said second fastener element and is adapted to hold said second fastener element within said third lumen.

9. The apparatus of claim 8, where said second needle includes a slot through said third lumen.

10. The apparatus of claim 1, where said second fastener element includes a tubular body along the length of said second body, where said tubular body includes a third lumen, where said second fastener element holding device includes a second needle, where said second needle has a second tip, and where said second needle is sized to accept said third lumen.

11. An apparatus comprising:
    a surgical suture including
    a first fastener element having a first proximal and a first distal end, where said first fastener element includes a first body having a first lumen between said first proximal end and said first distal end, and a first plurality of locking elements disposed between said first proximal end and said first distal end and which protrude away from said first body,
    a second fastener element including a second body having a second lumen between a second proximal end and a second distal end, and a second plurality of locking elements disposed between said second proximal end and said second distal end within said second lumen, and
    a length of suture having a first end attached to said first fastener element and a second end attached to said second fastener element; and
    a surgical suture holding device including
    a first fastener element holding device including a first needle, where said first needle has a first tip, where said first needle is sized to accept said first lumen, and
    a second fastener element holding device adapted to accept said second fastener element,
    where, with said first needle placed through said first lumen, and when said distal end of said first fastener element is inserted into the distal end of said second lumen of said second fastener element, said first plurality of locking elements interact with said second plurality of locking elements to inhibit movement of said first fastener element from said second fastener element.

12. The apparatus of claim 11, where said first fastener element holding device is configured to locate said first fastener element at a specific location in said first fastener element holding device.

13. The apparatus of claim 11, where said second fastener element holding device is configured to locate said second fastener element at a specific location in said second fastener element holding device.

14. The apparatus of claim 11, where said first plurality of locking elements are equally spaced along said first body, where said second plurality of locking elements are equally spaced along an inner surface of said second lumen with the same spacing as said first plurality of locking elements.

15. The apparatus of claim 11, where said first end of said suture is attached to either said proximal end of said first fastener element or said distal end of said first fastener element, and where said second end of said suture is attached to either said proximal end of said second fastener element or said distal end of said second fastener element.

16. The apparatus of claim 15, where said first end of said suture is attached to said proximal end of said first fastener element and where said second end of said suture is attached to said proximal end of said second fastener element.

17. The apparatus of claim 15, where said first end of said suture is attached to said distal end of said first fastener element and where said second end of said suture is attached to said proximal end of said second fastener element.

18. The apparatus of claim 11, where said second fastener element holding device includes a second needle having a third lumen adapted to accept said second fastener element.

19. The apparatus of claim 18, where said second needle includes a slot through said third lumen.

20. The apparatus of claim 11, where said second fastener element includes a tubular body along the length of said second body, where said tubular body includes a third lumen, where said second fastener element holding device includes a second needle, where said second needle has a second tip, and where said second needle is sized to accept said third lumen.

21. A method of suturing using a surgical suture including a first fastener element including a first body having a first lumen extending from a first proximal end to a first distal end, and a first plurality of locking elements protruding away from said first body, a second fastener element including a second body having an outer surface and a second lumen extending from a second proximal end and a second distal end, and a second plurality of locking elements within said second lumen, and a length of suture having a first end attached to said first fastener element and a second end attached to said second fastener element, said method further using a first fastener element holding device including a first needle sized to fit within said first lumen and a second fastener element holding device sized to hold said second fastener element, said method including:

inserting the first needle of the first fastener element holding device through the first lumen of the first fastener element;

accepting the second fastener element in the second fastener element holding device; inserting the first needle of the first fastener element holding device into the body of a patient;

moving said first fastener element holding device towards said second fastener element holding device, such that the first plurality of locking elements interact with said second plurality of locking elements to inhibit movement of said first fastener element from said second fastener element; and removing the surgical suture from the first fastener element holding device and the second fastener element holding device.

22. The method of claim 21, where said second fastener element holding device includes a second needle including a third lumen sized to accept the second body of the accepted second fastener element, where said third lumen is sized to accept said first needle and said accepted first fastener element, and where said second needle includes a slot for accepting the suture, where said accepting the second fastener element of the surgical suture in the second fastener element holding device includes inserting the second body of the surgical suture in the third lumen of the second fastener element holding device with the suture placed through the slot, the method further including inserting the second needle into the body of the patient.

23. The method of claim 21, where said second fastener element includes a tubular body having a third lumen, where said second fastener element holding device includes a second needle sized to fit through said third lumen, where said accepting the second fastener element of the surgical suture in the second fastener element holding device includes inserting the second needle through the third lumen, the method further including inserting the second needle into the body of the patient.

24. The method of claim 21, where said suturing is the suturing of a subfascial, a fascial, or intra-arterial wound.

\* \* \* \* \*